United States Patent
Zhang et al.

(10) Patent No.: US 9,458,119 B2
(45) Date of Patent: Oct. 4, 2016

(54) PROCESS FOR PRODUCTION OF DFMB DERIVATIVES

(75) Inventors: Tao Zhang, Shanghai (CN); Claude Mercier, Shanghai (CN); Olivier Buisine, Saint Fons (FR)

(73) Assignee: RHODIA OPERATIONS, Paris (FR)

( * ) Notice: Subject to any disclaimer, the term of this patent is extended or adjusted under 35 U.S.C. 154(b) by 92 days.

(21) Appl. No.: 14/377,056

(22) PCT Filed: Feb. 20, 2012

(86) PCT No.: PCT/CN2012/071346
§ 371 (c)(1),
(2), (4) Date: Aug. 6, 2014

(87) PCT Pub. No.: WO2013/123634
PCT Pub. Date: Aug. 29, 2013

(65) Prior Publication Data
US 2015/0005505 A1    Jan. 1, 2015

(51) Int. Cl.
*C07D 235/10* (2006.01)
*C07D 277/64* (2006.01)
*C07D 263/56* (2006.01)

(52) U.S. Cl.
CPC ........... *C07D 277/64* (2013.01); *C07D 235/10* (2013.01); *C07D 263/56* (2013.01)

(58) Field of Classification Search
USPC ..................................................... 548/310.4
See application file for complete search history.

(56) References Cited

U.S. PATENT DOCUMENTS

| | | | |
|---|---|---|---|
| 3,890,344 A | 6/1975 | Horlein et al. | |
| 4,122,184 A * | 10/1978 | Soper ..................... | A01N 43/52 514/394 |
| 2004/0224953 A1 | 11/2004 | Cowart et al. | |
| 2007/0244110 A1 * | 10/2007 | Yaguchi ............. | A61K 31/5377 514/232.8 |
| 2011/0218103 A1 * | 9/2011 | Frackenpohl .......... | A01N 43/52 504/103 |
| 2012/0165309 A1 | 6/2012 | Takahashi et al. | |
| 2012/0208811 A1 | 8/2012 | Taka et al. | |

FOREIGN PATENT DOCUMENTS

| | | |
|---|---|---|
| CN | 1760185 A | 4/2004 |
| CN | 1760184 A | 4/2006 |
| CN | 101012204 A | 8/2007 |
| CN | 101016274 A | 8/2007 |
| CN | 101016276 A | 8/2007 |
| JP | H 1045735 A | 2/1998 |
| WO | 97/10219 A1 | 3/1997 |
| WO | 2008/032077 A1 | 3/2008 |
| WO | WO 2008032064 A1 | 3/2008 |
| WO | 2010/092962 A2 | 8/2010 |
| WO | 2010/110685 A2 | 9/2010 |
| WO | 2011/016528 A1 | 10/2011 |

OTHER PUBLICATIONS

Smith et al., Journal of the American Chemical Society, (Mar. 20, 1953), 75, pp. 1292-1294.*
Fenglian, G., et al—"One-pot synthesis of 2-trifluoromethyl and 2-difluoromethyl substituted benzo-1,3-diazoles", Tetrahedron Letters, Mar. 7, 2007, vol. 48, pp. 3251-3254, Elsevier; 4 pgs.

* cited by examiner

*Primary Examiner* — Laura L. Stockton

(57) ABSTRACT

A process for the production of a compound of formula (III) which comprises a step of reacting a compound of formula (I) with an excess amount of a compound of formula (II) in absence of aromatic solvent,

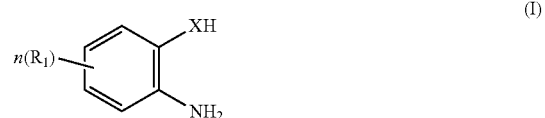

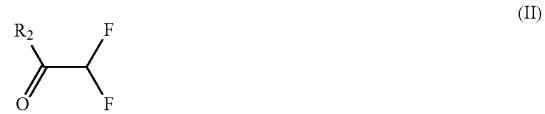

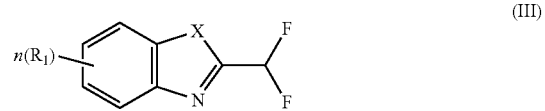

wherein n is 0, 1, 2, 3 or 4; X is NH, O or S; each $R_1$ group may be the same or different, and is independently selected from the group consisting of hydrogen, hydroxyl, alkoxy, alkyl, carbonyl, carboxyl, carboxylic acid ester, amido, cyano, halogenated aliphatic, nitro, and amino; and $R_2$ group is selected from the group consisting of hydroxyl, Cl, F, Br, amino, and alkoxy.

17 Claims, No Drawings

PROCESS FOR PRODUCTION OF DFMB DERIVATIVES

CROSS-REFERENCE TO RELATED APPLICATIONS

This application is a U.S. national stage entry under 35 U.S.C. §371 of International Application No. PCT/CN2012/071346 filed Feb. 20, 2012.

FIELD OF THE INVENTION

The invention relates to a process for production of DFMB (2-difluoromethyl-1H-benzimidazole) derivatives, particularly to a process for production of DFMB derivatives using DFAE (difluoroacetate ethyl) directly as solvent.

BACKGROUND OF THE INVENTION

DFMB derivatives are raw materials for an important new class of drugs, notably pharmaceutical intermediate and as potential anti HIV-1 bioactive.

WO2008032064 discloses a process for preparing DFMB (2-difluoromethyl-1H-benzimidazole) used as a starting material of pyrimidine derivatives or pharmaceutically acceptable salts thereof. It describes on page 99 of the description a process to produce DFMB in toluene with a yield of 77%, without the use of catalyst, at 87° C. and 41 h.

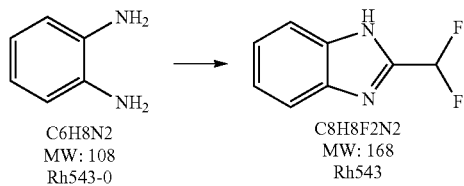 [SMILES: Nc1ccccc1N ; FC(F)c1nc2ccccc2[nH]1]

However, the process disclosed in WO2008032064 requires toluene as solvent and needs a very long reaction period, which is not environmental friendly and needs a relatively high cost. Therefore, there is still a need to develop a new process for preparing DFMB derivatives in the absence of aromatic solvent with a low cost.

SUMMARY OF THE INVENTION

The objective of the invention is to provide a new process of preparing DFMB derivatives with a low cost and without the use of aromatic solvent.

Thereby, the present invention relates to a process for the production of a compound of formula (III):

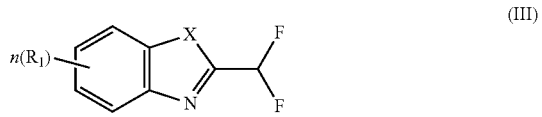

which comprises a step of reacting a compound of formula (I) with an excess amount of a compound of formula (II) in absence of aromatic solvent

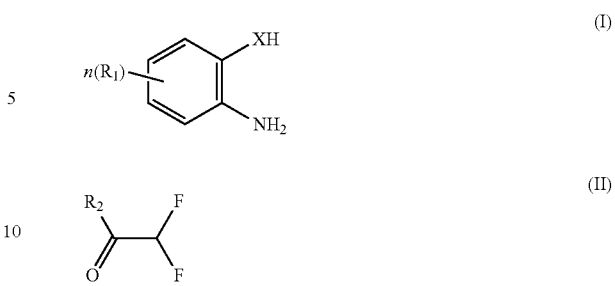

wherein
n is 0, 1, 2, 3 or 4;
X is NH, O or S;
each $R_1$ group may be the same or different, and is independently selected from the group consisting of hydrogen, hydroxyl, alkoxy, alkyl, carbonyl, carboxyl, carboxylic acid ester groups, amido, cyano, halogenated aliphatic, nitro, or amino groups;
$R_2$ group is selected from the group consisting of hydroxyl, Cl, F, Br, amino or alkoxy.

DETAILED DESCRIPTION OF THE INVENTION

Unless indicated otherwise, the term "DFMB derivatives" includes DFMB and its derivatives, as shown by formula (III).

Reacting a compound of formula (I) with an excess amount of a compound of formula (II) means that molar ratio of (II)/(I) is not less than 1, preferably not less than 2. According to some preferred embodiments, the molar ratio a compound of formula (II) to compound of formula (I) is from 2 to 10. According to some preferred embodiments, the molar ratio of the compound of formula (II) to the compound of formula (I) is 2-5.

According to some preferred embodiments, each $R_1$ may independently be hydrogen, hydroxyl, ($C_1$-$C_5$)alkoxy, ($C_1$-$C_5$)alkyl, carbonyl, carboxyl, carboxylic acid ester groups, amido, cyano, halogenated aliphatic groups, nitro, or amino. According to some preferred embodiments, at least one $R_1$ may independently be hydrogen, nitro, methoxyl group, or —COOEthyl. According to some preferred embodiments, halogenated aliphatic group may be perhalogenated aliphatic group, such as —$CF_3$ or —$CF_2Cl$.

In one preferred embodiment of the invention, the compound (I) is 1,2-phenylenediamine (orthophenylene diamine).

In one preferred embodiment of the invention, $R_2$ may be hydroxyl, Cl, F, Br, amino or ($C_1$-$C_5$) alkoxy. In further preferred embodiment of the invention, $R_2$ is ethoxy.

In one preferred embodiment of the invention, the compound (II) is difluoroacetate ethyl (DFAE) or difluoroacetic acid (DFA).

In one preferred embodiment of the invention, the compound (III) is 2,2-difluoromethyl 1H-benzimidazole (DFMB).

According to some embodiments of the invention, DFMB is prepared from 1,2-phenylenediamine and excess DFAE (difluoroacetate ethyl, also functions as solvent) without catalyst based on following equation:

1,2-phenylenediamine+DFAE→DFMB+EtOH+H₂O

According to some embodiments of the invention, DFMB is prepared from 1,2-phenylenediamine and excess DFA (difluoroacetic acid, also functions as solvent) without catalyst based on following equation:

1,2-phenylenediamine+DFA→DFMB+2H₂O

It is also possible to distillate continuously or not the co-product (water and/or alcohol) formed during the reaction; notably in order to displace the equilibrium faster and as such improve the volume productivity.

In the process of the invention, no aromatic solvent is used. Preferably, the compound of formula (II) is used as solvent and no additional solvent is added.

According to some preferred embodiments, the reaction medium comprising the excess compound of formula (II) is recycled at least partly and preferably wholly after the compound of formula (I) is fully reacted and the product of compound of formula (III) is removed.

According to the present process, the reaction can be completed in a very short time period. For example, when DFAE is used as the compound of formula (II) and as the sole solvent in the reaction system, DFMB can be prepared at 90° C. in 2-4 hours.

The process according to the present invention can be carried out in a one-pot process by cooling down the reaction system to make DFMB derivative product crystallize from the reaction system.

By the process of the present invention, the applicant surprisingly found that DFMB derivatives can be made in a relatively simple and inexpensive way. At first, the process does not need aromatic solvent which is not environmental friendly. More surprisingly, the process can be carried out without any additional solvent except the reactants. Secondly, the process, according to some embodiments of the invention, can surprisingly shorten the reaction period needed for completing the reaction to few hours, for example, 2 to 5 hours. Thirdly, the process does not need any catalyst but can still nearly achieve 100% conversion in short time period. Fourthly, pure DFMB derivatives can be crystallized from the reaction system by cooling down the reaction system. Therefore, the DFMB derivatives product can be separated from the reaction system by simple filtration, washing and drying to obtain highly pure product with a high yield. Moreover, the mother liquors containing the excess compound of formula (II), for example, DFAE, can be recycled to a new batch process. More surprisingly, a molar ratio of 2-5 of the compound of formula (II) to the compound of formula (I) is generally sufficient to complete the reaction in a short time period.

The present invention provides a process which is very productive in terms of volume productivity (kgs product/m³/hrs) and generates little or even no effluents because no catalyst is added and no extra reagent/activator is needed.

EXPERIMENTAL PART

1. Recycle DFAE Process

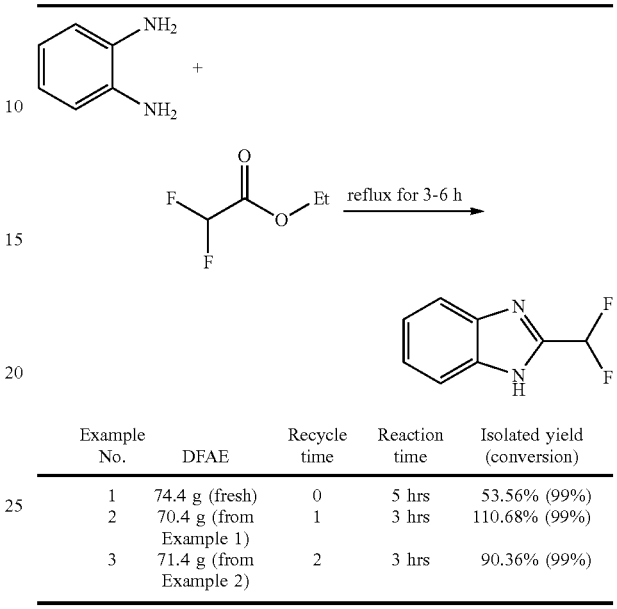

| Example No. | DFAE | Recycle time | Reaction time | Isolated yield (conversion) |
|---|---|---|---|---|
| 1 | 74.4 g (fresh) | 0 | 5 hrs | 53.56% (99%) |
| 2 | 70.4 g (from Example 1) | 1 | 3 hrs | 110.68% (99%) |
| 3 | 71.4 g (from Example 2) | 2 | 3 hrs | 90.36% (99%) |

Example 1

74.4 (0.6 mol) DFAE (ethyl 2, 2-difluoroacetate) was added to 21.6 g (0.2 mol) benzene-1, 2-diamine at room temperature under nitrogen. Then the mixture was heated to reflux (94-98° C.) and maintained for several hours under nitrogen. The mixture turned to blue clear solution gradually. After 5 hours the conversion of benzene-1, 2-diamine was >99% (determined by Gas Chromatography (GC)). The mixture was cooled down to 0° C., and solid was precipitated. After filtration, the obtained solid was washed with cool DFAE (17.4 g*3), and dried under vacuum. 18 g light green solid was obtained in 53.56% yield with 99% GC purity. Total 70 g filtrate (DFAE) and DFMB solubilized within DFAE were recycled and used in example 2.

Example 2

70.0 g DFAE (Recycled from example 1) was added to 21.6 g (0.2 mol) benzene-1,2-diamine at room temperature under nitrogen. Then the mixture was heated to reflux (94-98° C.) and maintained for several hours under nitrogen. The mixture turned to blue clear solution gradually. After 3 hrs the conversion of benzene-1,2-diamine was >99% (GC). The mixture was cooled down to 0° C., and solid was precipitated. After filtration, the obtained solid was washed with cool DFAE (17.4 g*3), and dried under vacuum. 37.2 g light green solid was obtained in 110.68% yield with 99% GC purity. Total 71.4 g filtrate (DFAE) and DFMB solubilized within DFAE were recycled for example 3.

Example 3

71.4 g DFAE (recycled from example 2) was added to 21.6 g (0.2 mol) benzene-1,2-diamine at room temperature under nitrogen. Then the mixture was heated to reflux (98-100° C.) and maintained for several hours under nitrogen. The mixture turned to blue clear solution gradually. After 3 hrs the conversion of benzene-1, 2-diamine was >99% (GC). The mixture was cooled down to 0° C., and solid was precipitated. After filtration, the obtained solid was washed with cool DFAE (17.4 g*3) and dried under vacuum. 30.37 g light green solid was obtained in 90.36% yield with 99% GC purity. Total 68.3 g filtrate (DFAE) was recycled.

In examples 1-3, total 85.57 g product was obtained in above 3 batches reactions and average yield for each experiment was 85.0%. Each product has a melting point of 162-163° C. The product was analyzed by 1H NMR and the spectrum was as follows:

1H NMR (300 MHz, DMSO-d6) δ: 7.16-7.42 (m, 3H), 7.68 (m, 2H), 13.3 (s, 1H). 19F NMR (282 MHz, DMSO-d6) δ: −115.98.

2. DFA Derivatives as Substrates

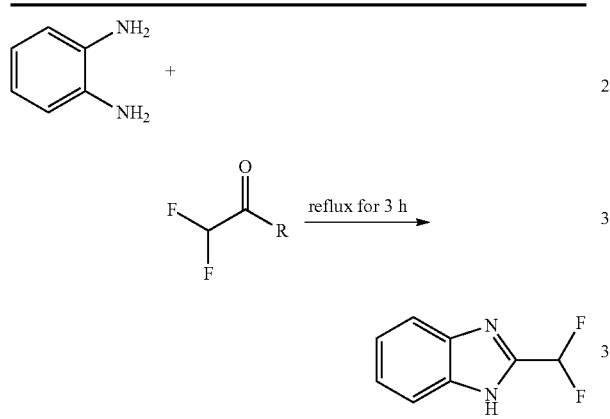

| Example No. | DFA derivative | Reaction time | Isolated yield (conversion) |
|---|---|---|---|
| 4 | F,F-CH-C(=O)-OH | 3 h | 74.87% (99%) |
| 5 | F,F-CH-C(=O)-O-iPr | 3 h | 64.3% (99%) * |
| 6 | F,F-CH-C(=O)-O-Me | 3 h | 50.3% (99%) * |
| 7 | F,F-CH-C(=O)-NH$_2$ | 3 h | 73.5% (99%) * |

(*) Low yield like in Example 1 as final product (III) stay in solvent at 0° C. (saturated solution) and these yields were not optimized.

Example 4

28.8 g (0.6 mol) DFA (2, 2-difluoroacetic acid) was added to 10.8 g (0.2 mol) benzene-1, 2-diamine at room temperature under nitrogen. Then the mixture was heated to reflux (94-98° C.) and maintained for 3 h under nitrogen. The mixture turned to blue clear solution gradually. After 3 h the conversion of benzene-1, 2-diamine was >99% (GC). The mixture was cooled down to room temperature, and neutralized by NaHCO$_3$ to pH=7-8. Some solid was precipitated, filtrated, washed with water, and then dried under vacuum at 45° C. 12.59 g white solid was obtained in 74.87% isolated yield.

Example 5

15.3 g (0.11 mol) DFAipr (isopropyl 2, 2-difluoroacetate) was added to 4.0 g (0.037 mol) benzene-1, 2-diamine at room temperature under nitrogen. Then the mixture was heated to reflux (98-100° C.) and maintained for 3 hrs under nitrogen. The mixture turned to blue clear solution gradually. After 19 hrs the conversion of benzene-1, 2-diamine was >99% (GC). The mixture was cooled down to 0° C., and solid was precipitated. After filtration, the obtained solid was washed with cool DFAipr for 3 times and dried under vacuum. 4 g light blue solid was obtained in 64.3% isolated yield.

Example 6

33.0 g (0.294 mol) DFAMe (methyl 2, 2-difluoroacetate) was added to 10.8 g (0.1 mol) benzene-1, 2-diamine at room temperature under nitrogen. Then the mixture was heated to reflux (98-100° C.) and maintained for 3 hrs under nitrogen. The mixture turned to blue clear solution gradually. After 3 hrs the conversion of benzene-1, 2-diamine was >99% (GC). The mixture was cooled down to 0° C., and solid was precipitated. After filtration, the obtained solid was washed with cool DFAMe for 3 times and dried under vacuum. 8.3 g light green solid was obtained in 50.3% isolated yield.

Example 7

27.84 g (0.294 mol) DFAN (2,2-difluoroacetamide) was added to 10.8 g (0.1 mol) benzene-1, 2-diamine at room temperature under nitrogen. Then the mixture was heated to reflux (120° C.) and maintained for several hours under nitrogen. The mixture turned to blue clear solution gradually. After 3 h the conversion of benzene-1, 2-diamine was 87.23% (GC). The mixture was cooled down to 0° C., and 300 ml EA was added. The organic phase was washed with 100 ml*4 water, and then with brine 50 ml*2. Dried with Na$_2$SO$_4$, removed solvent, 12.1 g orange solid was obtained in 73.5% isolated yield.

3. Diamine Derivatives as Substrates

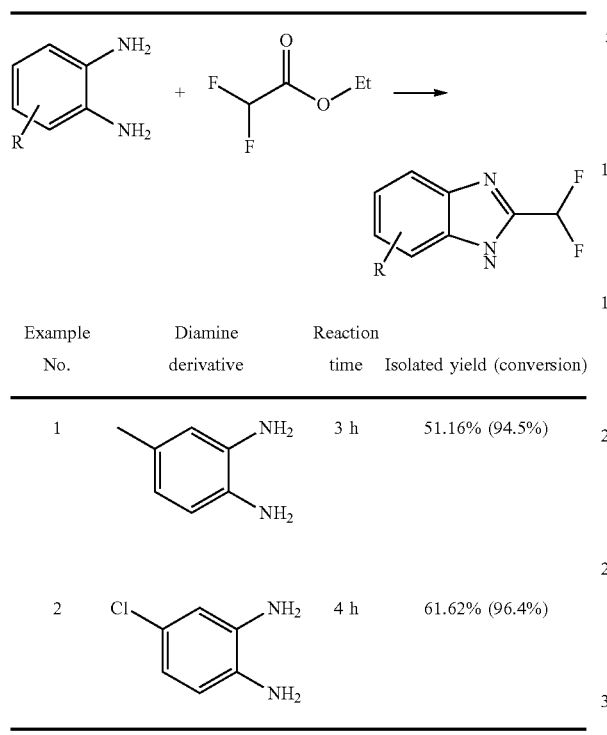

| Example No. | Diamine derivative | Reaction time | Isolated yield (conversion) |
|---|---|---|---|
| 1 | (4-methylbenzene-1,2-diamine) | 3 h | 51.16% (94.5%) |
| 2 | (4-chlorobenzene-1,2-diamine) | 4 h | 61.62% (96.4%) |

Example 8

37.2 g (0.3 mol) was added to 12.22 g (0.1 mol) 4-methylbenzene-1, 2-diamine at room temperature under nitrogen. Then the mixture was heated to reflux (98-100° C.) and maintained for 3 hrs under nitrogen. The mixture turned to blue clear solution gradually. After 3 hrs the conversion of 4-methylbenzene-1, 2-diamine was 94.5% (GC). The mixture was cooled down to 0° C., and solid was precipitated. After filtration, the obtained solid was washed with cool DFAE and dried under vacuum. 9.32 g light green solid was obtained in 51.16% isolated yield. mp: 152-153° C. 1H NMR (300 MHz, DMSO-d6) δ: 2.48 (s, 3H), 7.08-7.68 (m, 4H), 13.16 (s, 1H). 19F NMR (282 MHz, DMSO-d6) δ: −114.79.

Example 9

18.61 g (0.15 mol) DFAE was added to 7.13 g (0.05 mol) 4-chlorobenzene-1, 2-diamine at room temperature under nitrogen. Then the mixture was heated to reflux (98-100° C.) and maintained for 4 hrs under nitrogen. After 4 hrs the conversion of 4-chlorobenzene-1,2-diamine was 96.4% (GC). The mixture was cooled down to 0° C., and solid was precipitated. After filtration, the obtained solid was washed with cool DFAE, and dried under vacuum. 6.2 g light brown solid was obtained in 61.62% isolated yield with 99% GC purity. mp: 155-157° C. 1H NMR (300 MHz, CDCl3) δ: 7.16-7.42 (m, 2H), 7.67-7.74 (m, 2H), 13.53 (s, 1H). 19F NMR (282 MHz, CDCl3) δ: −115.91.

4. 2-Aminobenzenethiol as Substrate

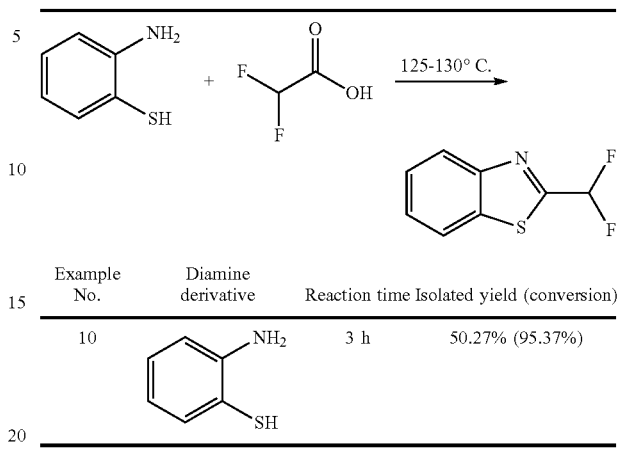

| Example No. | Diamine derivative | Reaction time | Isolated yield (conversion) |
|---|---|---|---|
| 10 | (2-aminobenzenethiol) | 3 h | 50.27% (95.37%) |

Example 10

28.80 g (0.3 mol) DFA (2,2-difluoroacetic acid) was added to 12.5 g (0.1 mol) 2-aminobenzenethiol at room temperature under nitrogen. Then the mixture was heated to reflux (125-130° C.) and maintained for 3 hrs (monitored by GC-MS). 2.4 g water was separated out with dean-stark. Then the mixture was cooled to room temperature, neutralized by NaHCO₃ in ice bath to pH=7-8, and some gray solid was precipitated from the solution. Separated by filtration, the cake was washed with water (20 ml*3) and dried under vacuum at room temperature. 9.3 g blue solid was obtained in 50.27% yield (GC conversation of 2-aminobenzenethiol: 95.37%). mp: 39-41° C. 1H NMR (300 MHz, DMSO-d6) δ: 7.38-7.70 (m, 3H), 8.20 (m, 1H), 8.26 (m, 1H). 19F NMR (282 MHz, DMSO-d6) δ: −113.08.

All documents cited in the Detailed Description of the Invention are, in relevant part, incorporated herein by reference.

It should be understood that every numerical range given throughout this specification will include every narrower numerical range that falls within such broader numerical range, as if such narrower numerical ranges were all expressly written herein.

All parts, ratios and percentages herein, in the specification, examples and claims, are by weight and all numerical limits are used with the normal degree of accuracy afforded by the art, unless otherwise specified.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for the production of a compound of formula (III):

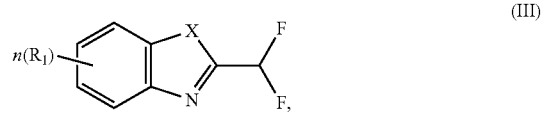

comprising a step of reacting a compound of formula (I) with an excess amount of a compound of formula (II) in absence of an aromatic solvent and in the absence of catalyst or extra reagent or activator

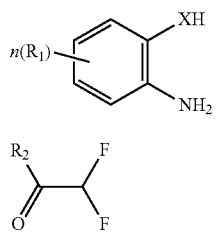
(I)

(II)

wherein
n is 0, 1, 2, 3 or 4;
X is NH, O or S;
each $R_1$ group, being the same or different, is independently selected from the group consisting of hydrogen, hydroxyl, alkoxy, alkyl, carboxyl, carboxylic acid ester groups, amido, cyano, halogenated aliphatic, nitro, and amino groups; and
said $R_2$ group is selected from the group consisting of Cl, F, Br, amino, and alkoxy;
wherein the step of reacting is carried out with a molar ratio of said compound of formula (II) to said compound of formula (I) from 2 to 5.

2. The process according to claim 1, wherein each $R_1$ is independently selected from the group consisting of hydrogen, hydroxyl, $(C_1-C_5)$alkoxy, $(C_1-C_5)$alkyl, carboxyl, carboxylic acid ester groups, amido, cyano, halogenated aliphatic groups, nitro, and amino groups.

3. The process according to claim 1, wherein at least one $R_1$ is independently selected from the group consisting of hydrogen, nitro, methoxyl, and —COOEthyl.

4. The process according to claim 1, wherein at least one $R_1$ group is a halogenated aliphatic group being a perhalogenated aliphatic group.

5. The process according to claim 4, wherein the perhalogenated aliphatic group is —$CF_3$ or —$CF_2Cl$.

6. The process according to claim 1, wherein the compound (I) is 1,2-phenylenediamine.

7. The process according to claim 1, wherein $R_2$ is selected from the group consisting of Cl, F, Br, amino, and $(C_1-C_5)$ alkoxy.

8. The process according to claim 1, wherein $R_2$ is ethoxy.

9. The process according to claim 1, wherein the compound (II) is difluoroacetate ethyl.

10. The process according to claim 1, wherein the compound (III) is 2-difluoromethyl-1H-benzimidazole.

11. The process according to claim 1, wherein said compound of formula (I) is fully reacted; and wherein said product of compound of formula (III) is removed to form a reaction medium comprising excess compound of formula (II) which is at least partly recycled.

12. The process according to claim 11, wherein said reaction medium comprising the excess compound of formula (II) is wholly recycled after the compound of formula (I) is fully reacted and the product of compound of formula (III) is removed.

13. The process according to claim 1, wherein the compound of formula (II) is used as solvent in said step of reacting.

14. The process according to claim 13, wherein no additional solvent is added in said step of reacting.

15. The process according to claim 1, wherein after said step of reacting, the compound (III) is crystallized by cooling.

16. The process according to claim 1, further comprising distilling a co-product which is formed during the step of reacting, said co-product being water, an alcohol, or combination thereof.

17. The process according to claim 1, wherein the compound (I) is 2-aminobenzenethiol.

* * * * *